(12) United States Patent
Brown (10) Patent No.: US 8,828,207 B2
(45) Date of Patent: Sep. 9, 2014

(54) DEEP SEA PH SENSOR

(75) Inventor: Gregory C. Brown, Chanhassen, MN (US)

(73) Assignee: Honeywell International Inc., Morristown, NJ (US)

( * ) Notice: Subject to any disclaimer, the term of this patent is extended or adjusted under 35 U.S.C. 154(b) by 282 days.

(21) Appl. No.: 13/495,613

(22) Filed: Jun. 13, 2012

(65) Prior Publication Data

US 2013/0334044 A1 Dec. 19, 2013

(51) Int. Cl.
*G01N 27/403* (2006.01)
*G01N 27/414* (2006.01)

(52) U.S. Cl.
USPC ............ 204/433; 204/400; 204/416; 257/253

(58) Field of Classification Search
CPC ................ G01N 27/302; G01N 27/36; G01N 27/333–27/401; G01N 27/414–27/4148; G01N 27/403
USPC ........................................................ 257/253
See application file for complete search history.

(56) References Cited

U.S. PATENT DOCUMENTS

| | | | |
|---|---|---|---|
| 3,652,439 A | 3/1972 | Ben-Yaakov et al. | |
| 7,906,859 B2 * | 3/2011 | Yoshioka et al. | ............. 257/788 |
| 2010/0036213 A1 * | 2/2010 | Rieth | ............. 600/301 |
| 2012/0187000 A1 * | 7/2012 | Kahn et al. | ............. 205/782 |
| 2012/0273845 A1 | 11/2012 | Brown et al. | |

FOREIGN PATENT DOCUMENTS

| | | | | |
|---|---|---|---|---|
| EP | 0615125 | 9/1994 | | |
| EP | 2518483 | 10/2012 | | |
| EP | 2570803 | 3/2013 | | |
| JP | 05099897 | 4/1993 | | |
| JP | 10227759 | 8/1998 | | |
| JP | 10-261553 A | * | 9/1998 | ............. H01L 21/02 |

OTHER PUBLICATIONS

JPO computer-generated English language translation of Ogiwara et al. JP 10-261553 A, patent published Sep. 29, 1998.*
Ben-Yaakov et al., "High Pressure pH Sensor for Oceanographic Applications", "The Review of Scientific Instruments", Aug. 1968, pp. 1133-1138, vol. 39, No. 8.
Johnson et al., "Development of an Integrated ISFET pH Sensor for High Pressure Applications in the Deep-Sea", Sep. 2011, pp. 1-5.
Martz et al., "Testing the Honeywell Durafet for Seawater pH Applications", Feb. 2010, pp. 172-184.
"SeaFET Ocean pH Sensor", Feb. 2012, pp. 1-2.
Shitashima et al., "Application of Chemical Sensor to Oceanography: Development of Deep Sea pH Sensor using ISFET", Jul. 1997, pp. 1-11.
Intellectual Property Office, "Combined Search and Examination Report", "from Foreign Counterpart of U.S. Appl. No. 13/495,613", Aug. 8, 2013, pp. 1-6, Published in: GB.

* cited by examiner

*Primary Examiner* — Alex Noguerola
(74) *Attorney, Agent, or Firm* — Fogg & Powers LLC (57) ABSTRACT

Systems and methods are provided for a deep sea pH sensor. In one embodiment, a method for manufacturing a pH sensor comprises forming a sensor electrode in a working surface of a die wherein the sensor electrode is able to sense the pH of a liquid and forming at least one isolation groove around the sensor electrode on the working surface of the die, wherein the die has a wide street around the sensor electrode and the at least one isolation groove. The method further comprises mounting the die onto a base and securing a seal on the working surface in the wide street, wherein the seal surrounds the isolation groove, the seal sealing the liquid within the portion of the working surface of the die containing the sensor electrode and the isolation groove, when the pH sensor is subjected to high pressure.

20 Claims, 6 Drawing Sheets

DEEP SEA PH SENSOR

GOVERNMENT LICENSE RIGHTS

The U.S. Government may have certain rights in the present invention as provided for by the terms of Government Contract #N00014-10-1-0206 awarded by Monterey Bay Aquarium Research Institute (MBARI) & US Navy.

BACKGROUND

In conducting oceanographic research and predicting climate change, scientists seek to understand the relative change in ocean $CO_2$ levels over time. One of the most effective methods to sense ocean $CO_2$ level is by precisely measuring the pH levels in the ocean. Further, to accurately determine the pH levels in the ocean, it is desirable to know the $CO_2$ levels between the maximum ocean depth and at incremental levels up to the ocean surface. Because the ocean has areas that are nearly 7 miles deep, to measure pH at the maximum ocean depths, a pH sensor must be able to withstand the different pressure levels that exist between the maximum ocean depths and the ocean surface.

SUMMARY

The embodiments of the present disclosure provide systems and methods for a deep sea pH sensor and will be understood by reading and studying the following specification.

Systems and methods are provided for a deep sea pH sensor. In one embodiment, a method for manufacturing a pH sensor comprises forming a sensor electrode in a working surface of a die wherein the sensor electrode is able to sense the pH of a liquid and forming at least one isolation groove around the sensor electrode on the working surface of the die, wherein the die has a wide street around the sensor electrode and the at least one isolation groove. The method further comprises mounting the die onto a base and securing a seal on the working surface in the wide street, wherein the seal surrounds the isolation groove, the seal sealing the liquid within the portion of the working surface of the die containing the sensor electrode and the isolation groove, when the pH sensor is subjected to high pressure.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale but are drawn to emphasize specific features relevant to the exemplary embodiments.

DETAILED DESCRIPTION

In the following detailed description, reference is made to the accompanying drawings that form a part hereof, and in which is shown by way of illustrating specific illustrative embodiments. However, it is to be understood that other embodiments may be utilized and that logical, mechanical, and electrical changes may be made. Furthermore, the method presented in the drawing figures and the specification is not to be construed as limiting the order in which the individual steps may be performed. The following detailed description is, therefore, not to be taken in a limiting sense.

Embodiments described herein provide for a sensor capable of sensing pH at different ocean depths. These deep sea pH sensors are fabricated in a robust package that can withstand the different and large pressures of the ocean. To withstand the different pressures, the pH sensors are configured to reduce any hysteretic stresses on the sensor electrode caused by the pressure found at great ocean depths. Further, the pH sensors described herein are configured to reduce stagnant sea water on the sensor electrode which can cause corrosion and microorganism growth. This is accomplished by providing a large area on the sensor die for the sensor electrode in which the sea water can be flushed across.

Figure 1:
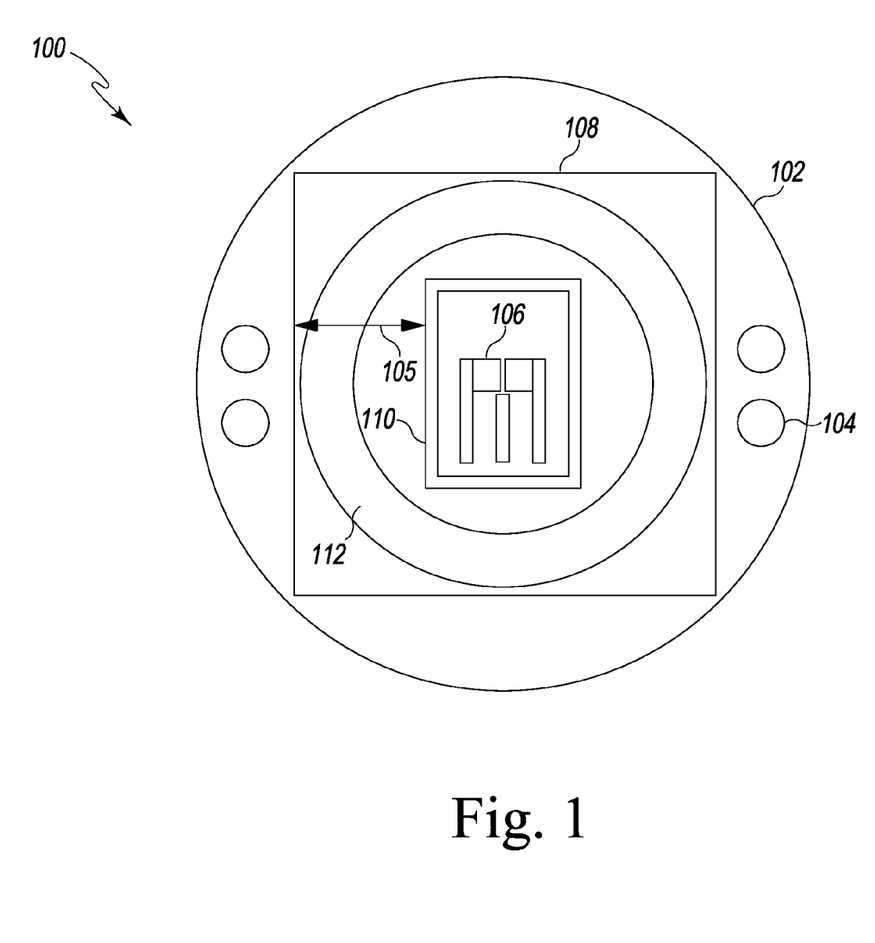
FIG. 1 is a block diagram of a top view of a sensor die according to one embodiment.

FIG. 1 is a block diagram that illustrates a top view of a sensor die 108 mounted on a base 102. The sensor die 108 is configured to sense the pH of liquids in contact with the sensor die 108. To sense the pH of liquids, the sensor die 108 includes a sensor electrode 106 formed in the top working surface of the sensor die 108. In at least one embodiment, sensor electrode 106 is a specialized MOSFET transistor. The gate of the MOSFET transistor responds to changes in the number of charged ions induced by changes in the pH of the liquid contacting a special ceramic coating on the MOSFET gate. As described in the present application, sensor die 108 can be implemented as a pH sensor capable of sensing the pH under the extreme pressures found at the bottom of the earth's oceans.

One difficulty in operating a pH sensor under extreme pressures is that the MOSFET transistor gate of the pH sensor is sensitive to changes in strain on its die. Cycling a conventional pH sensor from atmospheric pressure to extreme pressures, such as those found at the bottom of the earth's oceans, would cause hysteretic strain on the MOSFET transistor gate leading to inaccurate pH readings. This hysteretic strain can be caused by force from the packaging pressing onto the die including the MOSFET transistor gate.

To reduce hysteretic strain on the sensor electrode 106, the sensor die 108 includes an isolation groove 110 that is formed on sensor die 108 and is disposed between the sensor electrode 106 and a location in contact with the packaging of the sensor die 108. In the example shown in FIG. 1, the isolation groove 110 encircles the sensor electrode 106 and is disposed between the sensor electrode 106 and an extended portion 105 of the sensor die 108 that is subjected to pressure caused by the packaging of the sensor die 108. The isolation groove 110 comprises a trench in the top working surface of the sensor die 108. Since force on the extended portion 105 of the sensor die 108 can cause the sensor die 108 to deform and/or cause stress across the top working surface of the sensor die 108, the isolation groove 110 can reduce strain on the sensor electrode by providing a gap in the top working surface and thereby reducing the stress transfer along the top working surface from the extended portion 105 to the sensor electrode 106. The isolation groove 110 can be of any shape that encircles the sensor electrode 106 as long as the isolation groove 110 isolates strain applied to the surface of the extended portion 105 of the sensor die 108, thus inhibiting the strain from affecting the operation of the sensor electrode 106. In certain implementations, the extended portion 105 of the sensor die 108 has a width that increases the size of the sensor die 108 to be marginally larger than the size of the area encircled by the outer edge of the isolation groove 110. For example, in one embodiment, the area of the sensor die 108 encircled by the isolation groove 110 has the rectangular dimensions of 0.129 by 0.169 inches. The extended portion of the sensor die 108 increases the size of the sensor die beyond the isolation groove 110. In one exemplary implementation, the extended portion of the sensor die 108 increases the size of sensor die to have the rectangular dimensions of 0.34 inches by 0.325 inches. However, the extended portion of the sensor die can be as large as desired as the size of the die is constrained by the size of the isolation groove 110 formed on the top working surface of the sensor die 118 and manufacturing constraints and productivity requirements related to the fabrication of the sensor die on a wafer. In some alternative embodiments, the sensor die 108 does not have an isolation groove, and the extended portion 105 of the sensor die 108 extends between the sensor electrode 106 and the edge of the sensor die 108. When the sensor die does not have an isolation groove 110, the extended portion 105 of the sensor die has a width of at least 0.129 inches. The extended portion 105 of the sensor die 108 is formed by creating a wide street around the sensor electrode 106 and isolation groove 110 during fabrication of the sensor die 108. In certain embodiments, the extended portion 105 of the sensor die is blank, where blank indicates that there are no electronic devices formed thereon.

As sensor die 108 is part of a pH sensing device that is capable of operating underwater in the ocean, portions of the pH sensing device are unable to operate when contacted by seawater. For example, sensor die 108 is mounted on a base 102 that includes electrical bonding pads 104. The base 102 is manufactured from a rigid nonconductive material, such as a ceramic, a glass, and the like. The bonding pads 104 are standard bonding pads to one having skill in the art and are used for making electrical connections between different electrical components. For example, in one exemplary implementation, the bonding pads 104 provide an electrical connection between the sensor electrode 106 and the base 102 provide an electrical path for the measurements of the sensor electrode 106 to reach the rest of the pH sensing device and other electrical components to process the measurements. As salt water or other fluids would negatively affect the ability of the bonding pads 104 to reliably relay any electrical signals from the sensor electrode 106 and the salt water could damage other electrical components, the bonding pads and other electrical components of the pH sensing device are separated from the sensor electrode 106 by a seal 112. The seal 112 is a structure that seals off a portion of the pH sensing device from the liquid that contacts the sensor electrode 106. In an example, the seal 112 seals off some of the electronics of the pH sensor other than the sensor electrode 106, such that the sealed off electronics are not contacted by the liquid on the sensor electrode 106 which may damage, or provide a shorting path to, the sealed off electronics. The seal 112 is able to withstand the high pressure that exists in the ocean and extends around the isolation groove 110 and rests on the extended portion 105 of the sensor die 108. In one implementation the seal 112 includes an O-ring that has a substantially large enough diameter to allow enough space for the sensor electrode 106 and the isolation grooves 110 to reside within the O-ring. In a further implementation, the seal 112 includes a redundant set of concentrically arranged O-rings, where each O-ring has a large enough diameter to encircle the isolation groove 110. In an alternative embodiment, the seal 112 is formed by an epoxy that joins a rigid structure to the top working surface of sensor die 108.

Further, when the pH sensing device is in seawater, things like microorganisms and corrosion can occur when the seawater stagnates against the sensor electrode 106. The growth of microorganisms and corrosion can change the accuracy of the pH sensing device. Also, stagnant water resting against the sensor electrode 106 can negatively affect the ability of the sensor electrode 106 to accurately represent the pH of the seawater as local depletion of pH ions can affect the measurement. To reduce stagnation of fluid on the surface of the sensor electrode 106, the seal 112 exposes a large area of the sensor die 108 including and immediately around the sensor electrode 106 to an increase the flow of fluid in and out of the area. The extended portion 105 of the sensor die 108 enables the area to be larger than the sensor electrode 106 itself. In an example, an O-ring is at least 0.169 inches in diameter, and in a particular embodiment is greater than 0.120 inches in diameter. By providing a sensor die 108 with wide streets that surround an isolation groove 110 and a sensor electrode 106, the O-ring can be substantially large enough to allow flow across the sensor electrode 106 while facilitating operation of the pH sensing device in high pressure environments.

Figure 2:
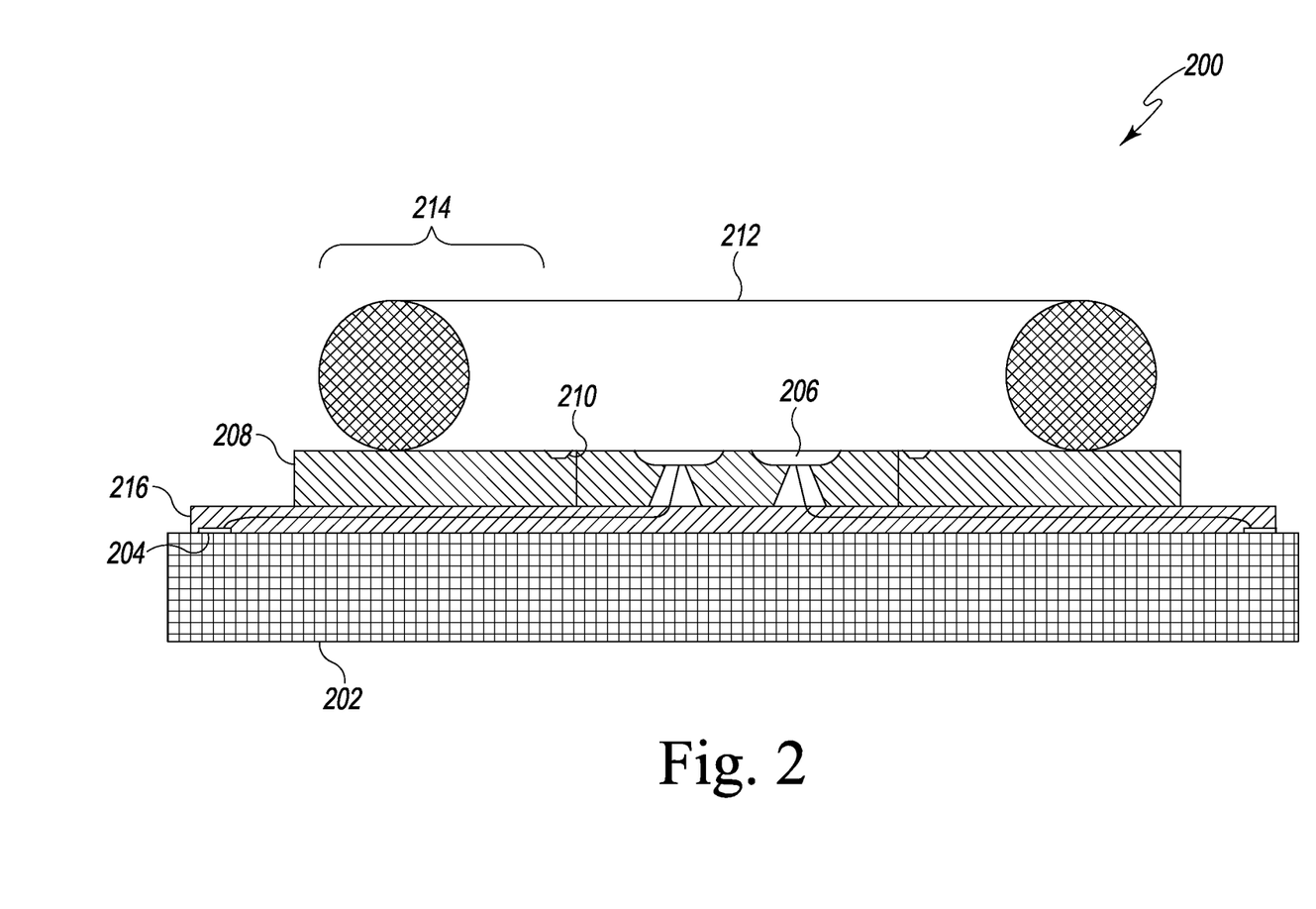
FIG. 2 is a block diagram of a cross sectional view of the sensor die with an attached O-ring according to one embodiment.

FIG. 2 is a block diagram of a cross sectional view of the pH sensor 200. The pH sensor 200 includes a sensor electrode 206 that functions similarly to sensor electrode 106 described above in relation to FIG. 1. The pH sensor 200 also includes an isolation groove 210 that functions similarly to isolation groove 110 as described above in relation to FIG. 1. As shown here, the isolation groove 210 and the sensor electrode 206 are formed in the sensor die 208. As illustrated, the sensor electrode 206 includes electrical contacts that extend through the sensor die 208 so that electrical connections can be made through the back side of sensor die 208 which isolates the electrical connections from the liquid that flows across surface of sensor electrode 206.

In certain embodiments, when multiple sensor dies 208 are fabricated on a single wafer, instead of using narrow streets between the multiple sensor dies 208 to maximize yield from the wafer, wide streets 214 are formed between the multiple sensor dies 208 formed on the wafer. Upon singulation of the multiple sensor dies 208 from the single wafer, a sensor die 208 has an extended surface area that is able to support a large O-ring 212 that both allows for liquid to flow across the surface of the sensor electrode 206 and encircle the isolation groove 210. In at least one implementation, a diverting structure is formed on the surface of sensor die 208 that directs the flow across sensor electrode 206.

As discussed above, the isolation groove 210 prevents pressure that is applied to the sensor die 208 from affecting the ability of the sensor electrode 206 to accurately sense the pH of the liquid that contacts the sensor electrode 206. For example, pressure is applied to O-ring 212 which then exerts a force on the sensor die 208. The force exerted on the sensor die 208 causes stress in the surface of sensor die 208. The stress extends through sensor die 208 except for the area enclosed by the isolation groove 210. Isolation groove 210 extends through a portion of sensor die 208 but not through the entire thickness of the sensor die 208. For example, if the sensor die was 0.2 inches thick, the isolation groove would extend 0.0001 to 0.15 inches through the sensor die 208. The isolation groove 210 absorbs the stress induced by O-ring 212 on the surface of the sensor die 208. In certain embodiments, the isolation groove 210 has beveled edges to minimize currents that could cause fluid to become stagnant within the isolation groove 210. In alternative embodiments, the isolation groove 210 has straight edges, such as those formed through deep reactive ion etching.

In at least one embodiment, the sensor die 208 is bonded to a base 202. The base 202 is substantially similar to the base 102 described in relation to FIG. 1. To bond the sensor die 208 to the base 202, a bonding agent is used that bonds both the sensor die 208 to the base 202 while providing enough space between the sensor die 208 and the base 202 for electrical connections to extend from the sensor electrode 206 to the bonding pads 204, where the bonding pads 204 function similarly to the bonding pads 104 described above in relation to FIG. 1. In at least one implementation, the sensor die 208 is bonded to base 202 with a bonding layer 216. When forming the bonding layer 216, wires are placed that extend through the bonding layer 216 while connecting the sensor electrode 206 to the bonding pads 204. In one example, the bonding layer 216 is made using a frit or other rigid material.

Figure 3:
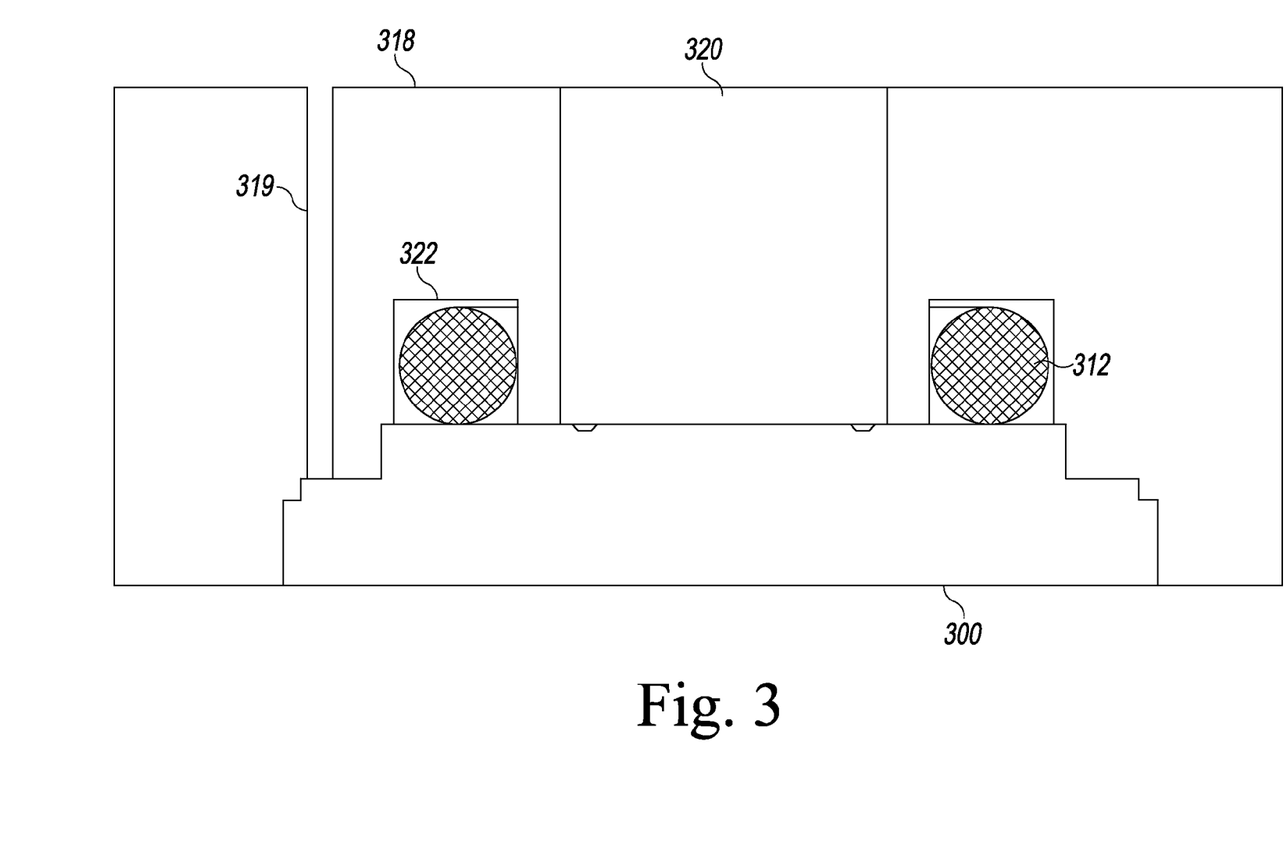
FIG. 3 is a block diagram of a cross sectional view of the sensor die with an attached sealing package according to one embodiment.

FIG. 3 is a block diagram of a cross sectional view of the pH sensor 300 with a pressure containment cover 318 attached to an O-ring 312. As illustrated, the combination of the O-ring 312 and the pH sensor 300 are similar to the O-ring 212 and the pH sensor 200 described above in relation to FIG. 2. The pressure containment cover 318 is designed to secure the O-ring 312 in a particular location on the surface of the pH sensor 300. For example, the pressure containment cover 318 includes an O-ring groove 322 that matches the diameter of the O-ring 312 and secures the O-ring 312 at a location around the isolation groove when the pressure containment cover 318 is subjected to pressure in a high pressure environment such as is encountered in a deep ocean environment. The pressure containment cover 318 is designed to contain the pressure around the base of the pH sensor 300 and isolate the pressure inside the pH sensor 300 from the pressure experienced by the sensor electrode 206 in FIG. 2. For example, the pressure containment cover 318 maintains the pressure inside the pH sensor 300 at or near the pressure at the surface of the ocean (subject to changes in pressure caused by cooling of the pH sensor due to ocean depths) while the pressure experienced by the sensor electrode and the exterior of the pressure containment cover 318 can be many times larger than 1 atmosphere. In one embodiment, pressure containment cover 318 includes an electrical connection conduit 319 that provides for electrical connections between the pH sensor 300 and other electrical devices near the pH sensor 300 such as a computing device that receives and processes the pH measurements from pH sensor 300.

In at least one embodiment, the pressure containment cover 318 includes an aperture 320 that allows fluid to continuously flow across the sensor electrode 206 without impeding the flow of the fluid. In one implementation, the pressure containment cover 318 and the aperture 320 are directly exposed to a liquid environment, where the fluid in the environment flows through the aperture 320 to flow across the pH sensor. When the fluid flows across the exterior of the pH sensor, a portion of the fluid will pass through the aperture 320 in the pressure containment cover 318 and flow across sensor electrode 206, where the pH sensor 300 measures the pH of the liquid in the environment. However, when the fluid in the environment is not flowing across the exterior of the pH sensor, fluid will likewise not flow across the sensor electrode 206. Due to the lack of moving water on the exterior of the pressure containment cover 318, fluid may stagnate on the surface of the sensor electrode 206, which stagnation may encourage contamination build up on the sensor electrode 206 and encourage the growth of microorganisms that can alter pH measurements.

Figure 4:
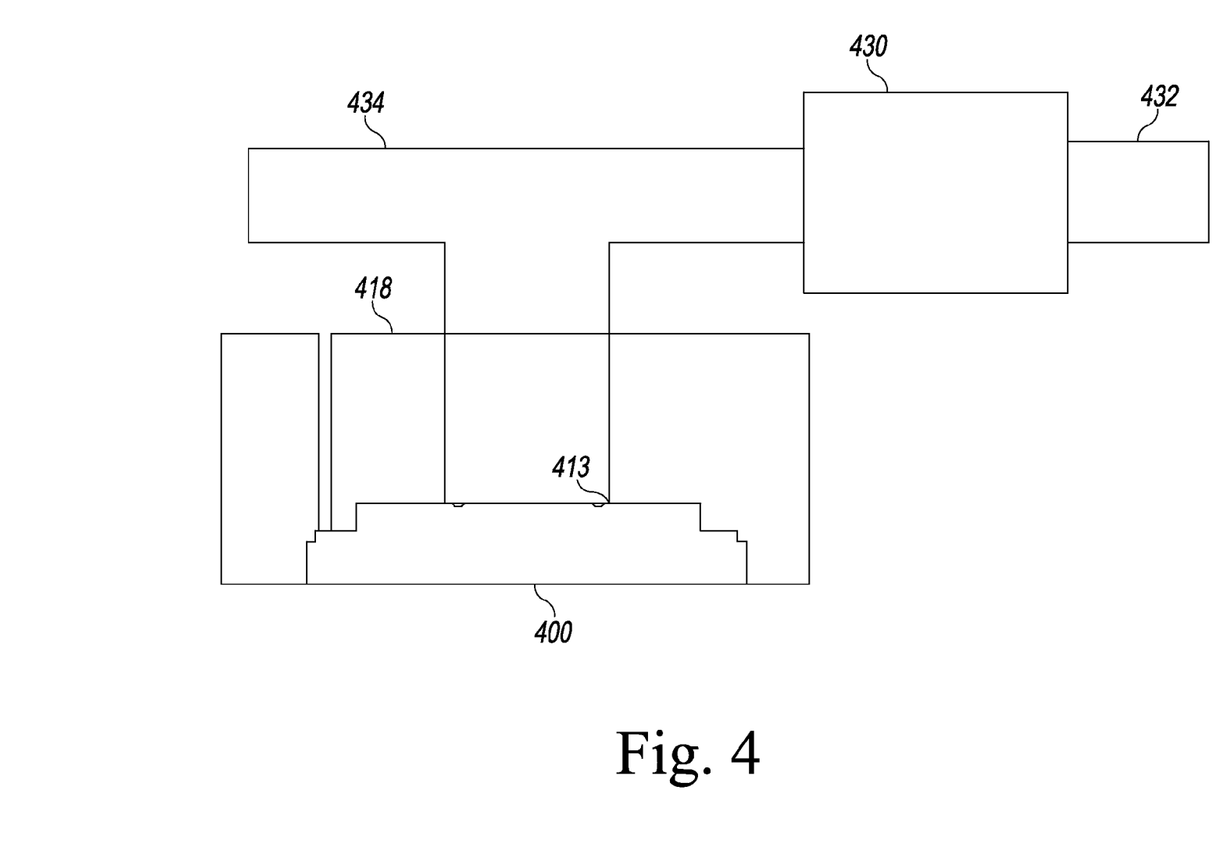
FIG. 4 is a block diagram of a pH sensor die with a flow mechanism that forces liquid to continuously flow across a sensing surface of the pH sensor die according to one embodiment.

FIG. 4 is a block diagram of a pH sensor 400 with a flow mechanism 430 that forces liquid to continuously flow across a sensing surface of the pH sensor die. As shown, flow mechanism 430 is a device like a pump that forces water to flow through the aperture in the pressure containment cover 418 and into the area within pressure containment cover, flow across the sensor electrode on pH sensor 400, and back out into the environment of the pH sensor 400. As shown in FIG. 4, pH sensor 400 is substantially similar to pH sensor 300 as described in relation to FIG. 3. However, pressure containment cover 418 seals directly to pH sensor 400 through an epoxy 413 that seals the pressure containment cover 418 to the working surface of the sensor die on pH sensor 400. In certain implementations, flow mechanism 430 includes two ports, an environment port 432 and a sensor port 434. Where the environment port 432 connects the flow mechanism 430 with the environment of the pH sensor 400 and the sensor port 434 connects the flow mechanism 430 with the pH sensor 400.

In certain embodiments, when flow mechanism 430 is a pump, the flow mechanism 430 can be a push pump or a pull pump. When flow mechanism 430 is a push pump, the flow mechanism 430 draws fluid from the environment through environment port 432 and pushes the fluid into the sensor port 434. In certain implementations, sensor port 434 is shaped like a "T" such that sensor port 434 has one straight section and a stub section that extends away towards the pH sensor 400 oriented at a 90 degree angle in relation to the straight section. When flow mechanism 430 is a push pump, the flow mechanism 430 primarily pushes the fluid through the straight section where eddies form in the stub section. The eddies that form in the stub section cause the fluid to flow across the sensor electrode of the pH sensor 400. In an alternative implementation, where flow mechanism 430 is a pull pump, the flow mechanism 430 draws fluid from the environment through the sensor port 434 and pushes the fluid into the environment through the environment port 432. When the flow mechanism 430 is a pull pump, the fluid is drawn through the straight section of the sensor port 434 directly from the environment. Similar to the push pump, when flow mechanism 430 is a pull pump, fluid is primarily pulled through the straight section where eddies form in the stub section. The eddies that form in the stub section cause the fluid to flow across the sensor electrode of the pH sensor 400. In certain embodiments, the pull pump may provide some advantages over the push pump, because, with the pull pump, the fluid passes over the sensor electrode before it passes through the pump. By passing over the sensor electrode before the pump, the pump is unable to alter the pH of the fluid.

Figure 5:
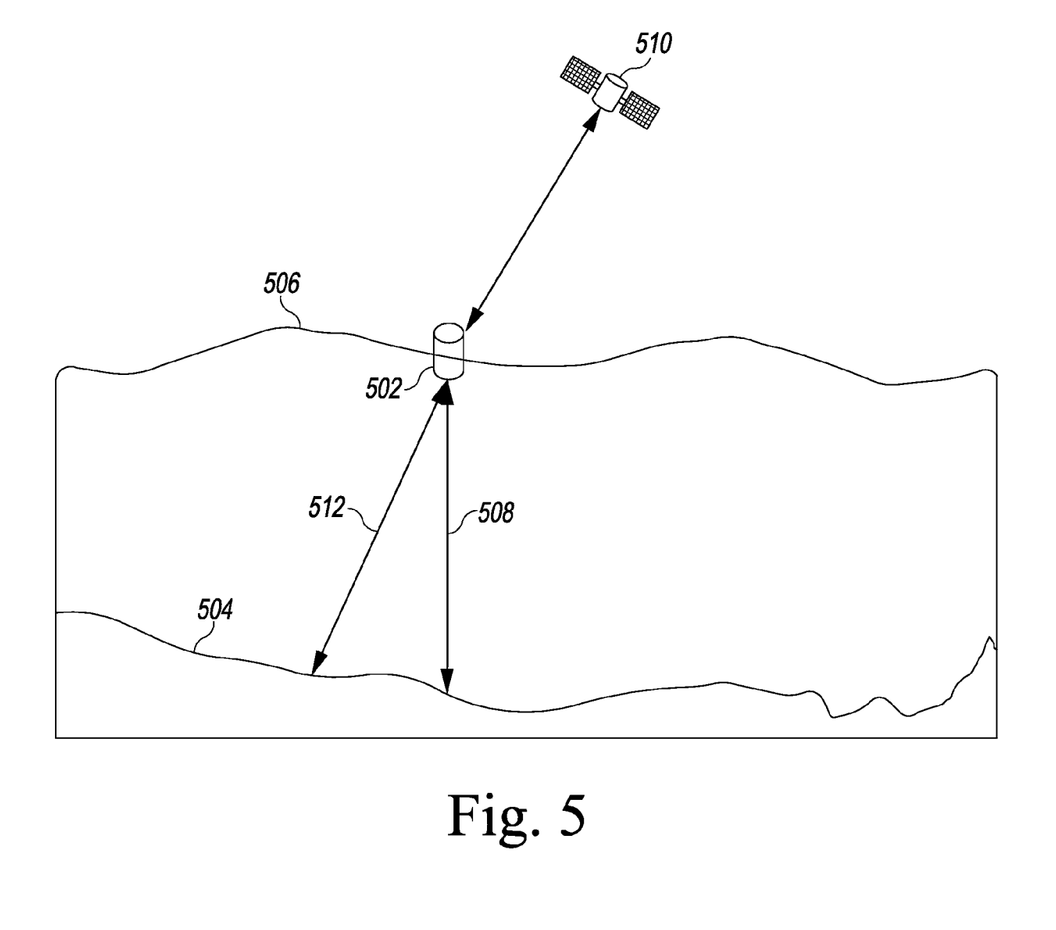
FIG. 5 is a diagram illustrating a buoy that gathers pH measurements in a body of water according to one embodiment.

FIG. 5 is a diagram illustrating a buoy 502 equipped with a pH sensor as described above that gathers pH measurements in a body of water. There are systems currently deployed within the earth's oceans that contain over 12,000 automated ocean buoys distributed over the area of the world's oceans that monitor several seawater parameters, however these buoys do not measure pH due to the lack of pH sensors that can reliably and capably measure pH at ocean depths up to seven miles. As illustrated in FIG. 5, a buoy 502 is equipped with a pH sensor. In certain embodiments, buoy 502 is in a body of water. Buoy 502 descends to the floor 504 of the body of water and primarily rests on the floor 504 of the body of water. Periodically, buoy 502 ascends to the surface 506 of the body of water. When the buoy 502 ascends to the surface 506, the buoy travels along an ascent path 508 and incrementally gathers measurements as it travels along the ascent path 508 from the floor 504 to the surface 506. When the buoy 502 reaches the surface 506, the buoy 502 transmits the gathered pH measurements to a data receiver 510. In certain implementations, the data receiver 510 is a satellite, but the data receiver 510 also includes communication systems located on a boat, on ground, in an aerial vehicle, and the like. The data receiver 510 then relays the data to another destination for analysis. After the buoy 502 transmits the pH measurements, the buoy 502 descends back to the floor 504 along descent path 512. In certain implementations, ascent path 508 and descent path 512 are identical. Alternatively, the ascent path 508 and descent path 512 are different. When the buoy 502 descends to the floor 504, the buoy 502 rests until the next time the buoy 502 is scheduled to ascend to surface 506 to gather pH measurements.

Figure 6:
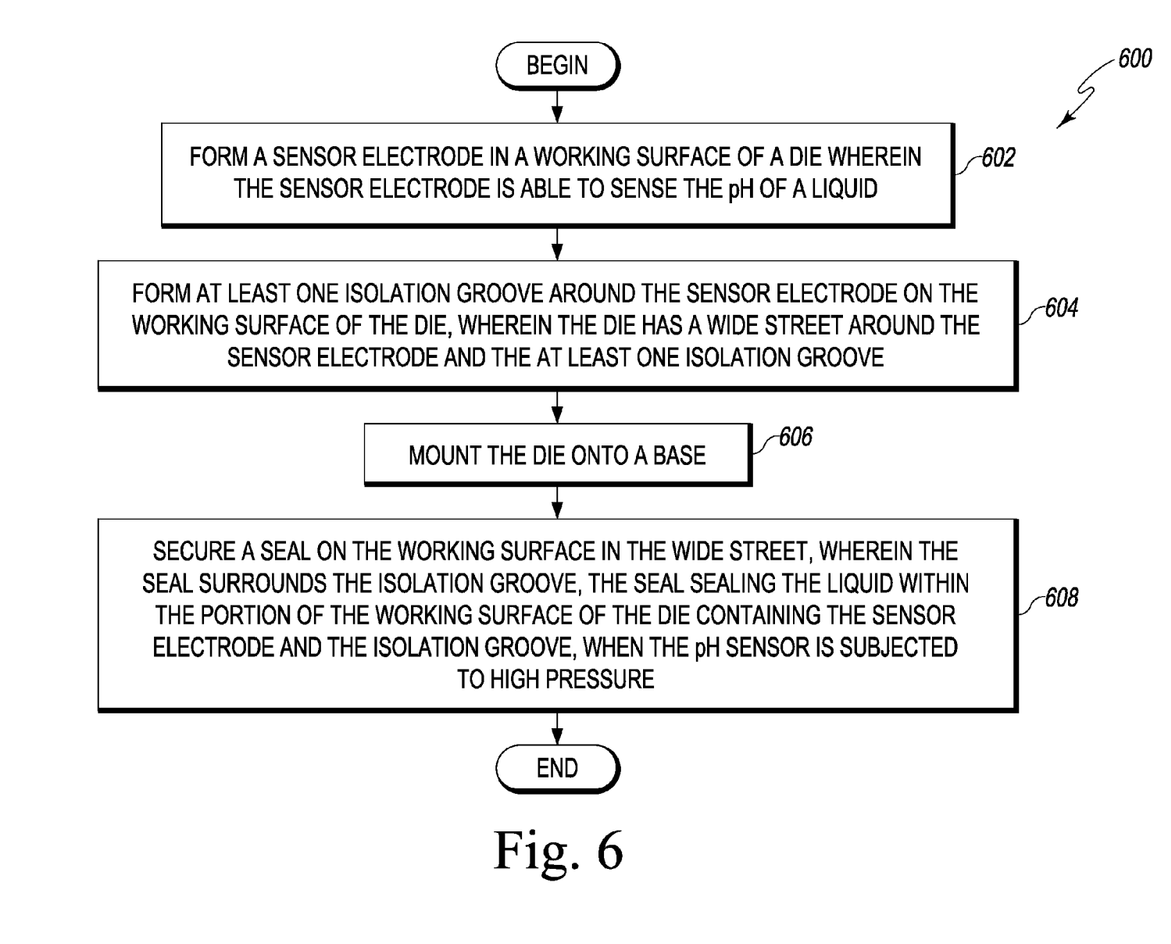
FIG. 6 is a flow diagram illustrating a method for fabricating a pH sensor according to one embodiment.

FIG. 6 is a flow diagram illustrating a method 600 for fabricating a pH sensor as described above in relation to FIGS. 1-5. At block 602, a sensor electrode is formed in a working surface of a die wherein the sensor electrode is configured to sense the pH of a liquid. For example, a MOSFET transistor that is capable of measuring pH is formed in a die that is part of a wafer containing multiple MOSFET transistors. At block 604, at least one isolation groove is formed around the sensor electrode on the working surface of the die, wherein the die has a wide street around the sensor electrode and the at least one isolation groove. In at least one exemplary implementation, an isolation groove is formed around the sensor electrode by masking the die such that an area encircling the sensor electrode is exposed and then etching the die to form a trench or groove that encircles the sensor electrode. In one implementation, the groove has beveled edges, while, alternatively, the groove can have straight edges. Further, when multiple sensor electrodes are formed in a wafer, the sensor electrodes and corresponding isolation grooves are separated from one another by wide streets such that multiple extended surface area dies are formed on the wafer.

In a further implementation, at block 606, the die is mounted onto a base. For example, a die containing a sensor electrode, an isolation groove, and an extended surface area is joined to the base. In at least one implementation the base is a ceramic and the die is joined to the base through the application of a frit or other bonding material. Also, the sensor electrode is electrically connected to bonding pads formed on the base. In the implementations where there are multiple sensor electrodes formed on a wafer, the wafer is singulated into separate dies such that each die has an extended surface area or wide street that surrounds the sensor electrode and isolation groove.

In certain embodiments, at block 608, a seal is secured on the working surface in the wide street, wherein the seal surrounds the isolation groove, the seal sealing the liquid within the portion of the working surface of the die containing the sensor electrode and the isolation groove, when the pH sensor is subjected to high pressure. For instance, an O-ring is placed on the extended surface area, where the O-ring encircles the sensor electrode and the isolation groove. Further, a pressure containment cover is placed over the O-ring to secure the O-ring in place on the extended surface area of the die. When the pressure containment cover experiences external pressure, the O-ring is pressed between the pressure containment cover and the die. Because the O-ring is pressed into the surface of the die, the isolation groove prevents the stress on the die induced by the O-ring from affecting the operation of the sensor electrode.

EXAMPLE EMBODIMENTS

Example 1 includes a pH sensor, comprising a base; a sensor electrode formed on a working surface of a die, wherein the die is mounted to the base, wherein the sensor electrode is configured to sense the pH of a liquid when in contact with the liquid; a high pressure seal in contact with the working surface, the high pressure seal configured to isolate liquid to the working surface of the die when the pH sensor is subjected to high pressure; and at least one isolation groove formed around the sensor electrode on the working surface of the die, wherein the at least one isolation groove is configured to isolate the sensor electrode from stress produced by the high pressure seal on the working surface when the pH sensor is subjected to high pressure.

Example 2 includes the pH sensor of Example 1, wherein the high pressure seal comprises an O-ring in contact with the working surface of the die, wherein the O-ring encircles the at least one isolation groove; and a sealing cover configured to secure the O-ring on the extended surface area when the pH sensor is subjected to high pressure.

Example 3 includes the pH sensor of Example 2, wherein the O-ring is mounted on an extended portion of the die that extends around the at least one isolation groove on the surface of the die.

Example 4 includes the pH sensor of any of Examples 2-3, wherein the sensor electrode is less than 0.16 inches across at a widest portion and the diameter of the O-ring is at least 0.16 inches.

Example 5 includes the pH sensor of any of Examples 1-4, further comprising a pump configured to force the liquid to continuously flow across the sensor electrode.

Example 6 includes the pH sensor of Example 5, wherein the pump is configured as at least one of a push pump; and a pull pump.

Example 7 includes the pH sensor of any of Examples 1-6, wherein the die is mounted to the base using a bonding layer.

Example 8 includes the pH sensor Examples 7, wherein the sensor electrode is electrically connected to wirebonds on the base that are embedded in the bonding layer.

Example 9 includes the pH sensor of any of Examples 7-8, wherein the bonding layer is composed of frit.

Example 10 includes a method for manufacturing a pH sensor, the method comprising forming a sensor electrode in a working surface of a die wherein the sensor electrode is able to sense the pH of a liquid; forming at least one isolation groove around the sensor electrode on the working surface of the die, wherein the die has a wide street around the sensor electrode and the at least one isolation groove; mounting the die onto a base; and securing a seal on the working surface in the wide street, wherein the seal surrounds the isolation groove, the seal sealing the liquid within the portion of the working surface of the die containing the sensor electrode and the isolation groove, when the pH sensor is subjected to high pressure.

Example 11 includes the method of Example 10, wherein forming the sensor electrode comprises forming the sensor electrode on a wafer containing a plurality of sensor electrodes; and singulating the wafer to form the die including the sensor electrode.

Example 12 includes the method of any of Examples 10-11, wherein the die is mounted to the base using a frit layer.

Example 13 includes the method of any of Examples 10-12, wherein the seal is at least one of at least one O-ring held in place by a pressure containment cover; and an epoxy that secures the pressure containment cover to the working surface of the die.

Example 14 includes the method of Example 13, wherein the O-ring encircles the at least one isolation groove and the sensor electrode.

Example 15 includes a pH sensing device, the device comprising a base; a die containing a sensor electrode and an isolation groove encircling the sensor electrode and formed on a working surface of the die, the die mounted to the base, wherein the sensor electrode is configured to sense the pH of a liquid when in contact with the liquid; an O-ring placed on the working surface of the die, wherein the O-ring encircles the isolation groove; a pressure containment cover configured to secure the O-ring on the working surface, such that the pressure containment cover and the O-ring configured to seal liquid that contacts the sensor electrode from the area of the working surface that is outside the inner diameter of the O-ring when the pH sensing device is subjected to high pressure; and a flow mechanism configured to force a fluid to continuously flow across the sensor electrode.

Example 16 includes the pH sensing device of Example 15, wherein the portion of the die on the working surface that is outside the inner diameter of the O-ring is blank.

Example 17 includes the pH sensing device of any of Examples 15-16, wherein the flow mechanism is a pump attached to the pressure containment cover.

Example 18 includes the pH sensing device of any of Examples 15-17, wherein the pH sensing device is mounted on a buoy in a body of water, the buoy configured to submerge in the water to depths up to 7 miles.

Example 19 includes the pH sensing device of Example 18, wherein the pH sensing device incrementally gathers pH measurements as the buoy travels from a bottom of the body of water to a surface of the body of water.

Example 20 includes the pH sensing device of Example 19, wherein the buoy transmits the pH measurements to data gathering system when the buoy is on the surface of the body of water.

A number of embodiments of the invention defined by the following claims have been described. Nevertheless, it will be understood that various modifications to the described embodiments may be made without departing from the spirit and scope of the claimed invention. Accordingly, other embodiments are within the scope of the following claims.

What is claimed is:

1. A pH sensor, comprising:
    a base;
    a sensor electrode formed on a working surface of a die, wherein the die is mounted to the base, wherein the sensor electrode is configured to sense the pH of a liquid when in contact with the liquid;
    a high pressure seal in contact with the working surface, the high pressure seal configured to isolate liquid to the working surface of the die when the pH sensor is subjected to high pressure; and
    at least one isolation groove formed around the sensor electrode on the working surface of the die, wherein the at least one isolation groove is configured to isolate the sensor electrode from stress produced by the high pressure seal on the working surface when the pH sensor is subjected to high pressure.

2. The pH sensor of claim 1, wherein the high pressure seal comprises:
    an O-ring in contact with the working surface of the die, wherein the O-ring encircles the at least one isolation groove; and
    a sealing cover configured to secure the O-ring on the extended surface area when the pH sensor is subjected to high pressure.

3. The pH sensor of claim 2, wherein the O-ring is mounted on an extended portion of the die that extends around the at least one isolation groove on the surface of the die.

4. The pH sensor of claim 2, wherein the sensor electrode is less than 0.16 inches across at a widest portion and the diameter of the O-ring is at least 0.16 inches.

5. The pH sensor of claim 1, further comprising a pump configured to force the liquid to continuously flow across the sensor electrode.

6. The pH sensor of claim 5, wherein the pump is configured as at least one of a:
    a push pump; and
    a pull pump.

7. The pH sensor of claim 1, wherein the die is mounted to the base using a bonding layer.

8. The pH sensor of claim 7, wherein the sensor electrode is electrically connected to wirebonds on the base that are embedded in the bonding layer.

9. The pH sensor of claim 7, wherein the bonding layer is composed of frit.

10. A method for manufacturing a pH sensor, the method comprising:
    forming a sensor electrode in a working surface of a die wherein the sensor electrode is able to sense the pH of a liquid;
    forming at least one isolation groove around the sensor electrode on the working surface of the die, wherein the die has a wide street around the sensor electrode and the at least one isolation groove;
    mounting the die onto a base; and
    securing a seal on the working surface in the wide street, wherein the seal surrounds the isolation groove, the seal sealing the liquid within the portion of the working surface of the die containing the sensor electrode and the isolation groove, when the pH sensor is subjected to high pressure.

11. The method of claim 10, wherein forming the sensor electrode comprises
    forming the sensor electrode on a wafer containing a plurality of sensor electrodes; and
    singulating the wafer to form the die including the sensor electrode.

12. The method of claim 10, wherein the die is mounted to the base using a frit layer.

13. The method of claim 10, wherein the seal is at least one of:
    at least one O-ring held in place by a pressure containment cover; and
    an epoxy that secures the pressure containment cover to the working surface of the die.

14. The method of claim 13, wherein the O-ring encircles the at least one isolation groove and the sensor electrode.

15. A pH sensing device, the device comprising:
    a base;
    a die containing a sensor electrode formed on a working surface of the die, the die mounted to the base, wherein the sensor electrode is configured to sense the pH of a liquid when in contact with the liquid;

an O-ring placed on the working surface of the die, the O-ring encircling the sensor electrode, wherein the O-ring has a diameter that is substantially large such that liquid can flow freely across the sensor electrode;

a pressure containment cover configured to secure the O-ring on the working surface, such that the pressure containment cover and the O-ring configured to seal liquid that contacts the sensor electrode from the area of the working surface that is outside the inner diameter of the O-ring when the pH sensing device is subjected to high pressure; and a flow mechanism configured to force a fluid to continuously flow across the sensor electrode.

16. The pH sensing device of claim 15, wherein the portion of the die on the working surface that is outside the inner diameter of the O-ring is blank.

17. The pH sensing device of claim 15, wherein the flow mechanism is a pump attached to the pressure containment cover.

18. The pH sensing device of claim 15, wherein the pH sensing device is mounted on a buoy in a body of water, the buoy configured to submerge in the water to depths up to 7 miles.

19. The pH sensing device of claim 18, wherein the pH sensing device incrementally gathers pH measurements as the buoy travels from a bottom of the body of water to a surface of the body of water.

20. The pH sensing device of claim 19, wherein the buoy transmits the pH measurements to data gathering system when the buoy is on the surface of the body of water.

* * * * *